(12) United States Patent
Efremkin

(10) Patent No.: US 11,344,369 B2
(45) Date of Patent: May 31, 2022

(54) LASER DEVICE FOR VASCULAR AND INTRABODY SURGERY AND METHOD OF USE

(71) Applicant: Pavel V. Efremkin, Ardsley, NY (US)

(72) Inventor: Pavel V. Efremkin, Ardsley, NY (US)

( * ) Notice: Subject to any disclaimer, the term of this patent is extended or adjusted under 35 U.S.C. 154(b) by 0 days.

(21) Appl. No.: 16/702,517

(22) Filed: Dec. 3, 2019

(65) Prior Publication Data
US 2020/0100839 A1    Apr. 2, 2020

Related U.S. Application Data

(63) Continuation-in-part of application No. 16/431,727, filed on Jun. 4, 2019.

(60) Provisional application No. 62/680,311, filed on Jun. 4, 2018.

(51) Int. Cl.
*A61B 18/24* (2006.01)
*A61B 18/00* (2006.01)
*A61B 18/22* (2006.01)

(52) U.S. Cl.
CPC .. *A61B 18/245* (2013.01); *A61B 2018/00029* (2013.01); *A61B 2018/00404* (2013.01); *A61B 2018/00577* (2013.01); *A61B 2018/00589* (2013.01); *A61B 2018/00625* (2013.01); *A61B 2018/00648* (2013.01); *A61B 2018/00702* (2013.01); *A61B 2018/00791* (2013.01); *A61B 2018/00994* (2013.01); *A61B 2018/2211* (2013.01)

(58) Field of Classification Search
CPC ........ A61B 18/245; A61B 2018/00029; A61B 2018/00404; A61B 2018/00577; A61B 2018/00589; A61B 2018/2211; A61B 2018/00648; A61B 2018/00702; A61B 2018/00791; A61B 2018/00994; A61B 2018/00625; A61B 2018/00601; A61B 2218/001; A61B 17/3401; A61B 17/3417
See application file for complete search history.

(56) References Cited

U.S. PATENT DOCUMENTS

| | | | | | |
|---|---|---|---|---|---|
| 3,877,429 | A | * | 4/1975 | Rasumoff | A61M 25/0668 604/158 |
| 4,585,437 | A | * | 4/1986 | Simms | A61M 25/013 604/106 |
| 5,571,215 | A | * | 11/1996 | Sterman | A61B 17/00234 128/898 |
| 2002/0077637 | A1 | * | 6/2002 | Vargas | A61F 2/064 606/153 |
| 2003/0199860 | A1 | * | 10/2003 | Loeb | A61B 18/24 606/17 |

OTHER PUBLICATIONS

International Search Report in corresponding International Application No. PCT/US 19/64387.

* cited by examiner

*Primary Examiner* — Nathan J Jenness
(74) *Attorney, Agent, or Firm* — Lawrence G. Fridman, Esq; Feigin & Fridman, LLC

(57) ABSTRACT

A laser atherectomy device includes a light delivery catheter equipped with sensors for monitoring physical characteristics at a laser application site. An integrated control unit utilizing data from said sensors is provided to optimally adjust laser energy parameters and to provide for safe and efficacious ablation of the blood vessel occlusion.

6 Claims, 12 Drawing Sheets

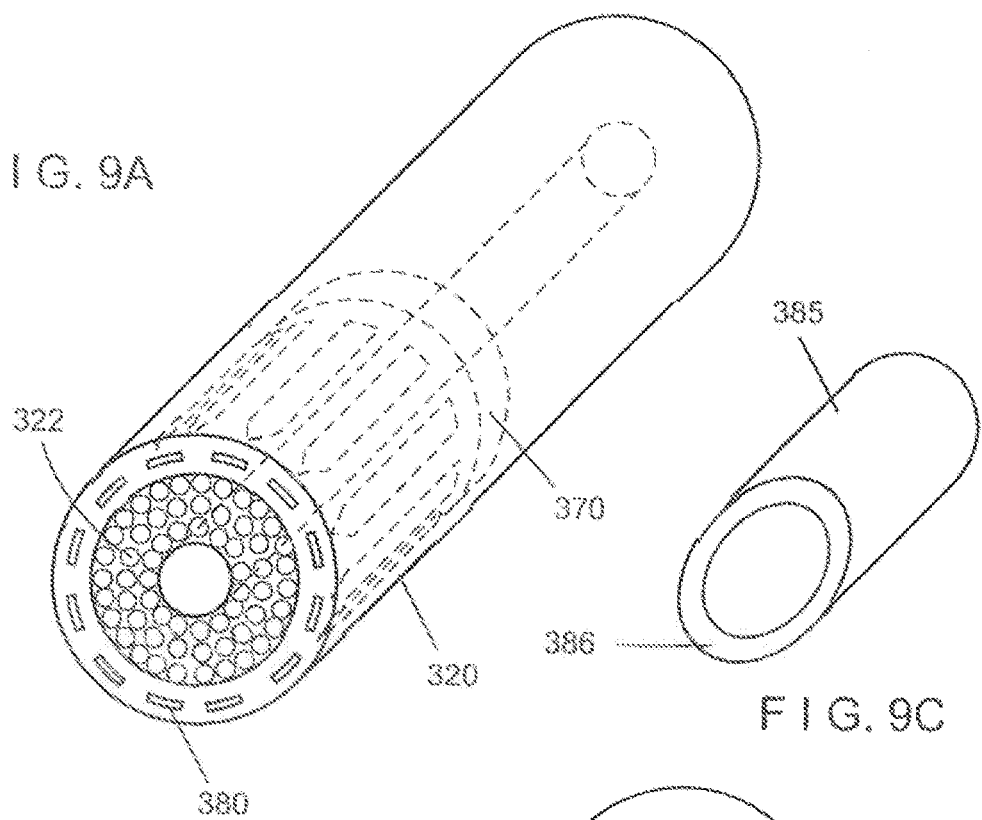
FIG. 9A
FIG. 9C
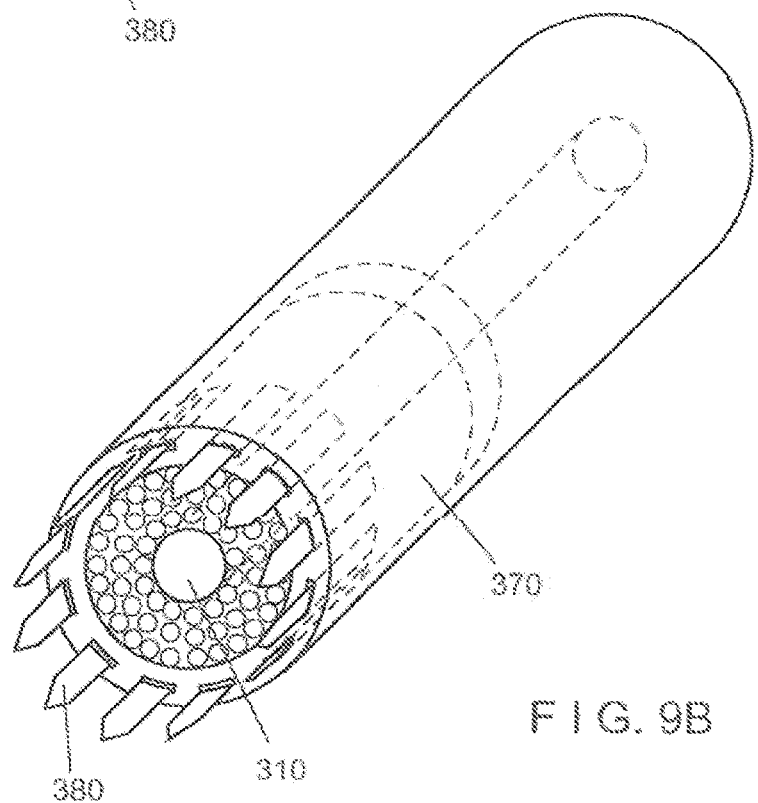
FIG. 9B

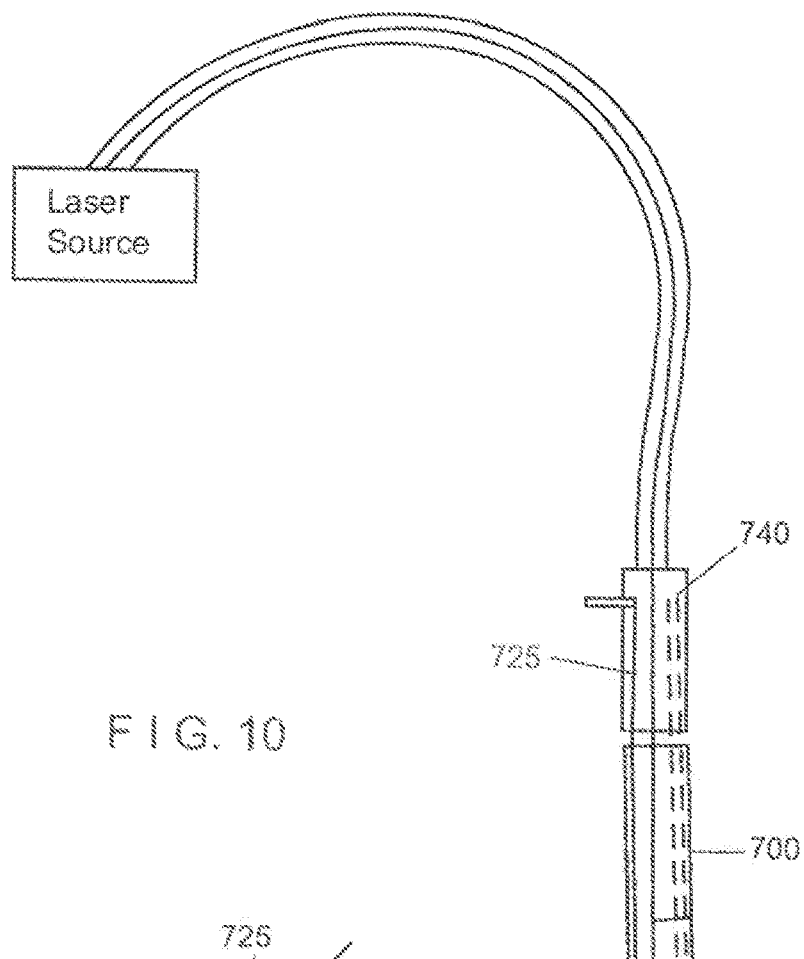
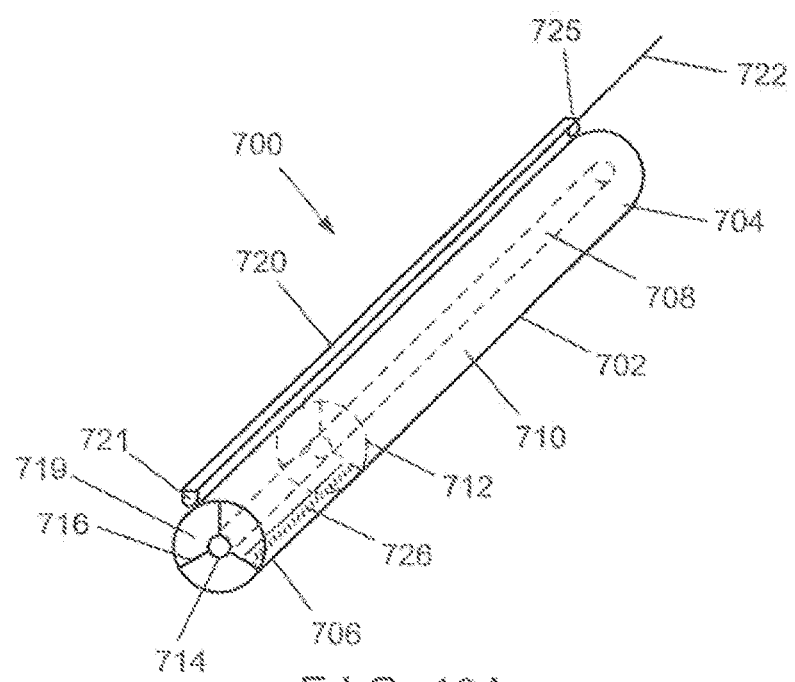
FIG. 10
FIG. 10A

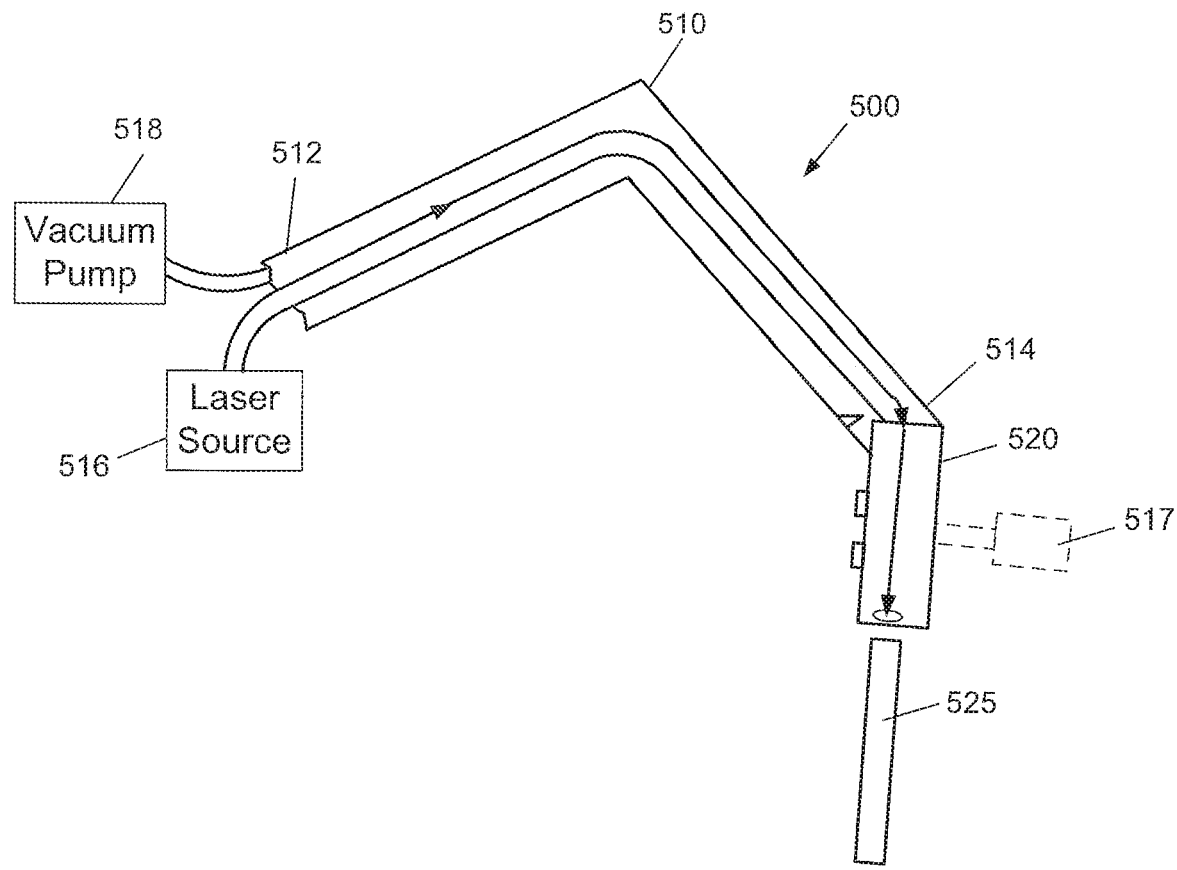
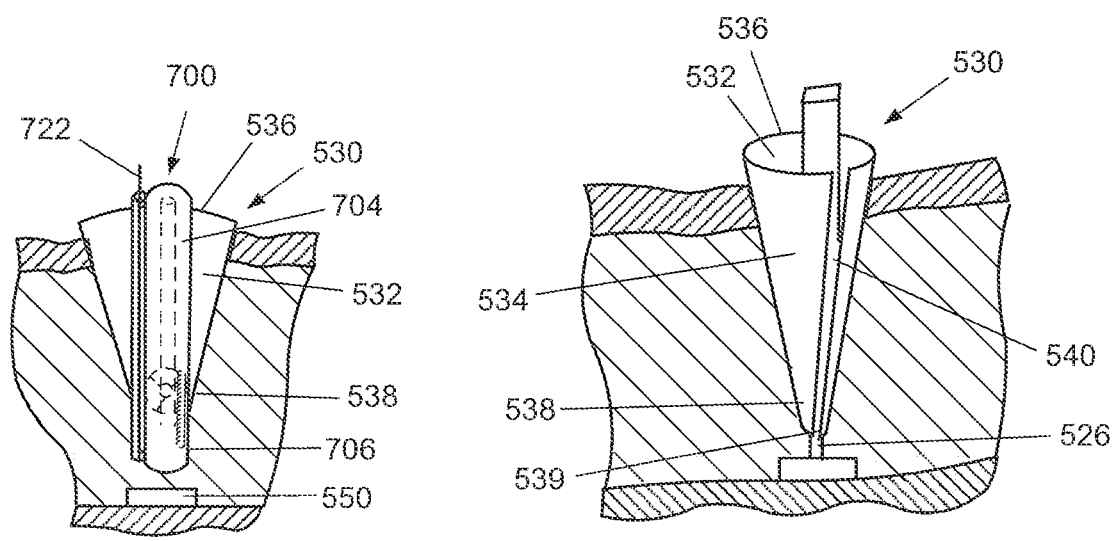
FIG. 11A                    FIG. 11

LASER DEVICE FOR VASCULAR AND INTRABODY SURGERY AND METHOD OF USE

CROSS-REFERENCE TO RELATED APPLICATION

The present application is a continuation-in-part application of currently pending application Ser. No. 16/431,727 filed Jun. 4, 2019 which claims priority of Provisional Patent Application Ser. No. 62/680,311 filed by the Applicant on Jun. 4, 2018, the entire disclosure of these applications is hereby incorporated by reference.

FIELD OF THE INVENTION

The devices and methods of the invention generally relate to intrabody surgery and to treatment of occluded body lumens. In particular, the invention relates to an improved laser system to optimally generate and deliver through catheters laser energy for use in the removal of the occluding material from the blood vessels as well as other body lumens.

BACKGROUND OF THE INVENTION

The laser system, devices and methods of the invention are applicable for various types of intrabody surgery including, but not limited to cutting, breaking, coagulation, vaporization of any body tissue (including but not limited to Soft tissue includes tendons, ligaments, fascia, skin, fibrous tissues, fat, and synovial membranes; and muscles, nerves and blood vessels (which are not connective tissue) as well as hard tissue/bone and connective tissue) which involves reaching the targeted tissue through body channels including but not limited to blood vessels, ureter, esophagus, stomach and duodenum (esophagogastroduodenoscopy), small intestine (enteroscopy), large intestine/colon (colonoscopy, sigmoidoscopy) or incision or cut through the body tissues (laparoscopic surgery).

Although laser system, devices and methods for removal of the occluding material from the blood vessels as well as other body lumens are discussed below in greater detail, it should be clear that these are some of many possible applications of the invention. Laser system, devices and methods of the invention are applicable to many types of intrabody surgery, as identified above including but not limited to general surgery, cardiology, orthopedic surgery, urology and gastroenterology surgery.

Cardiovascular diseases frequently arise from the accumulation of atheromatous material on the inner walls of vascular lumens, particularly arterial lumens of the coronary and other vasculature including coronary artery disease (CAD) build-up of plaque in the arteries of the heart, as well as peripheral artery disease (PAD)—a narrowing of the peripheral arteries serving the legs, stomach, arms and head, resulting in a condition known as atherosclerosis. Atheromatous and other vascular deposits restrict blood flow and can cause ischemia which, in acute cases, can result in myocardial infarction or a heart attack. Atheromatous deposits can have widely varying properties, with some deposits being relatively soft and others being fibrous and/or calcified. In the latter case, the deposits are frequently referred to as plaque. Atherosclerosis occurs naturally as a result of aging but may also be aggravated by factors such as diet, hypertension, heredity, vascular injury, and the like.

Atherosclerosis can be treated in a variety of ways, including drugs, bypass surgery, and a variety of catheter-based approaches which rely on intravascular widening or removal of the atheromatous or other material occluding the blood vessel. Catheter-based interventions include angioplasty, atherectomy, laser ablation, stenting, and the like. For the most part, the catheters used for these interventions are introduced over a guidewire, and the guidewire is placed across the lesion prior to catheter placement. Initial guidewire placement, however, can be difficult or impossible in tortuous regions of the vasculature. Moreover, it can be equally difficult if the lesion is total or near total, i.e. the lesion occludes the blood vessel lumen to such an extent that the guidewire cannot be advanced across the lesion.

Occlusion in a blood vessel can be caused by a variety of materials from hard bone like calcium deposits to soft blood clot or piece of fatty deposit. Multiple type occlusions may be present in the same vessel. Currently different tools are used to remove different types of occlusion. Surgeons may need to remove one type of catheter and replace it with another one in order to successfully work with different occlusion types. This extends treatment time, substantially raises cost, and increase risk for a patient. The inventions provide a more optimal and complete solution to this problem which includes means to analyze the type of occlusion material present and then adapt the function of the occlusion removal device accordingly.

In prior art, there are known rotational atherectomy systems utilizing diamond drill tips/burrs to sand hard-calcified occlusions to very small particles. While there are some discussions that the particles produced from 20 μm diamond-tipped burr that ablates plaque into micro-particles are smaller in size (~5 μm) than a red blood cell (8 μm), it is also known that larger particles of debris produced when occlusion is being broken are generated. Such larger particles can block blood capillaries and cause serious side effects. However, even when the occlusion particles are as small as blood cells, their presence in the blood stream may present a potential risk. This is especially so if such particles are accumulated at the essential body tissues causing malfunctioning of the vital body organs. Visible accumulation of even smaller particles, for example tattoo ink particles (less than 1 μm[9]), is very known. The tattoos particles accumulation (tattoo) is well known to be permanent or at least long term. Since the tattoo ink is inserted into the skin, it mostly stays in the dermis. Thus, impact of the ink particles on other tissue and organs is localized. On the other hand, since the particles generated during the occlusion destruction can be carried out through the blood stream to the vital body organs, proper management of such particles become important. Some of the rotational atherectomy catheters have built-in arrangements with active aspiration to remove debris from the blood stream and evacuate the debris through the catheter. However, these aspiration (debris evacuation) arrangements are not optimally designed to remove all or most of such debris particles. The inventions propose more optimal and complete solutions to this problem.

The prior art solutions for removal of calcium plaque are often provided with forwardly shaped rotational drills. Some of such prior art design presents a risk of accidental perforation of the blood vessel walls if such drill is pushed against the wall during the procedure. One of the aspects of the invention provides ways to limit such risks of vessel wall perforation as well as minimizes negative aspects of the procedure on any adjacent tissue.

SUMMARY OF THE INVENTION

One aspect of the invention provides apparatus for laser ablation of biological tissue which includes a hollow guide wire having one or more openings along the distal end to facilitate aspiration designed to be used to suck and remove debris of occlusion or embolus in the blood vessel. The guide wire made as a hollow tube designed to be used as a conduit for aspiration of occlusion debris produced by the laser energy applied to the occlusion material with such guide wire also having openings along the distal end to facilitate aspiration.

Another aspect of the invention provides alight delivery catheter for laser ablation of biological tissue provided to deliver light energy from a source to occlusion in the blood vessel. The light energy is emitted from the distal end of the light guide. The light energy destroys/affects/removes an occlusion in the blood vessel or a soft tissue in through vaporization, coagulation, cavitation or opto-acoustical waves, optical-chemical or other physical mechanisms of light interaction with a targeted tissue.

A further aspect of the invention provides a laser atherectomy device including a light delivery catheter equipped with sensors for monitoring physical characteristics at a laser application site. An integrated control unit utilizing data from the sensors is provided to optimally adjust laser energy parameters and to provide for safe and efficacious ablation of the blood vessel occlusion.

Still aspect of the invention provides a sterile package housing an atherectomy treatment catheter allowing conveniently drawing part of the catheter outside of the package for the intravenous application while keeping the rest of the catheter in sterile internal storage compartment; —with such package housing comprising of two reels capable of independently rotating and releasing catheter winded on each reel.

BRIEF DESCRIPTION OF THE DRAWINGS

In the following drawings, the same parts in the various views are afforded the same reference designators. Referring now to the drawings which are provided to illustrate and not to limit the invention, wherein:

FIGS. 9A, 9B and 9C are perspective views further illustrating application of the modified inflatable balloon combined with extendable blades of FIGS. 8A and 8B;

FIGS. 10 and 10A are the view illustrating a laser surgical device according to a further embodiment of the invention;

FIGS. 11 and 11A are the views illustrating a laser surgical system according to still another embodiment of the invention.

DETAILED DESCRIPTION OF THE INVENTION

The invention contemplates use of the energy sources known to one of ordinary skills in the medical profession for fragmenting, coagulating, or vaporizing various unwanted materials from a body lumen. In a preferred embodiment, the energy is laser energy with a wavelength that is highly absorbable in a water content medium. In this respect, the present invention contemplates use of a vast variety of lasers, including, but not limited to solid state lasers, diode lasers, gas lasers, semiconductor lasers, or broad band light source, etc. In the method of the invention light energy destroys/affects/removes occlusions in the blood vessels or a soft tissue in a certain desirable way. This includes vaporization, coagulation, cavitation or opto-acoustical waves, optical-chemical or other physical mechanisms of light interaction with a targeted tissue. The light energy is emitted from the distal end of the light guide.

In suitable laser systems, the energy of each pulse and the pulsation frequency can be varied. Generally, high frequency of pulsation and high energy produce a quick fragmentation but also produces an increase in temperature of in the treatment area as well as a significant amount of particle mobility. Lower frequency of pulsation and lower energy is more precise, but the overall treatment time is prolonged. High frequency of pulsation and high energy can be used by the devices of the present invention because active aspiration to remove debris from the blood stream/the suction force limits particle movement. By combining suction with a laser delivery system in accordance with the methods of the invention, the overall efficiency of treatment is improved. In addition the laser catheter in the current invention is equipped with a temperature sensor that monitor the temperature level at the treatment site which is used by the control unit of the laser system to optimally adjust laser energy parameters (such as frequency or repetition rate of laser pulses) to prevent overheating and thermal damage to the surrounding healthy tissue.

Figure 1:
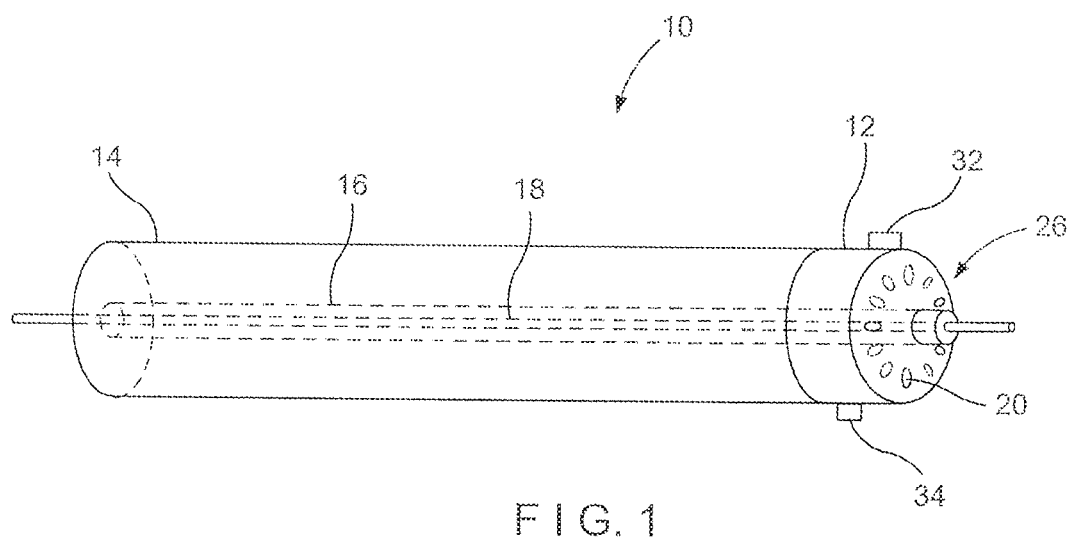
FIGS. 1 and 2 are diagrams illustrating a distal end of the light delivery catheter and various components of the invention.

As the energy emitted by the laser catheter contacts the undesirable bodily material within the subject's vascular system, it separates and cuts such material in a generally concentric configuration. This technique is also known as coring. And if the bodily material that is cut is substantially solid, it will appear as generally cylindrically looking core. Although FIG. 1 illustrates the laser emitters in a generally concentric configuration, those skilled in the art will appreciate that there are numerous other ways and configurations in which to arrange a plurality of laser catheter emitters. Accordingly, the system/arrangement of FIG. 1 discussed below, is not intended to represent the only way that a laser catheter may be configured and constructed, and all such configurations and constructions are within the knowledge of one skilled in the art are considered within the scope of this disclosure.

In the invention, alight delivery or laser catheter 10 is provided to deliver light energy from a source (laser, solid state laser, diode laser, gas laser, semiconductor laser of broad band light source) through (using) blood vessels (veins or arteries or other body channels) to a place in the body, where such light energy may destroy/affect/remove an occlusion in the blood vessel or a soft tissues by means of vaporization, coagulation, cavitation or opto-acoustical waves, optical-chemical or other physical mechanisms of light interaction with a targeted tissue. Such light is emitted from the distal end of the light guide. The light catheter of the invention is formed having size, thickness and mechanical and other properties suitable and convenient to use by the method of invention.

A "laser catheter emitter" refers to an end portion of a fiber or an optical component that emits laser light from a distal end of the catheter towards a desired target, which is typically tissue. An optical fiber (or laser active fiber) is a flexible, transparent fiber made of an optically transmissive material, such as glass (silica) or plastic that functions as a waveguide, or "light pipe", to transmit light between the two ends of the fiber.

A "coupler" or "fiber optic coupler" refers to the optical fiber device with one or more input fibers and one or several output fibers. Fiber couplers are commonly special optical fiber devices with one or more input fibers for distributing optical signals into two or more output fibers. Optical energy is passively split into multiple output signals (fibers), each containing light with properties identical to the original except for reduced amplitude.

One aspect of the invention provides a combination of laser emitters and mechanical cutting tips at the distal end used in conjunction with an aspiration system. Laser catheter transmits laser energy through optical fibers housed in a flexible tubular catheter inserted into a body lumen, such as a blood vessel, and the like to remove obstructions in the lumen.

Figure 2:
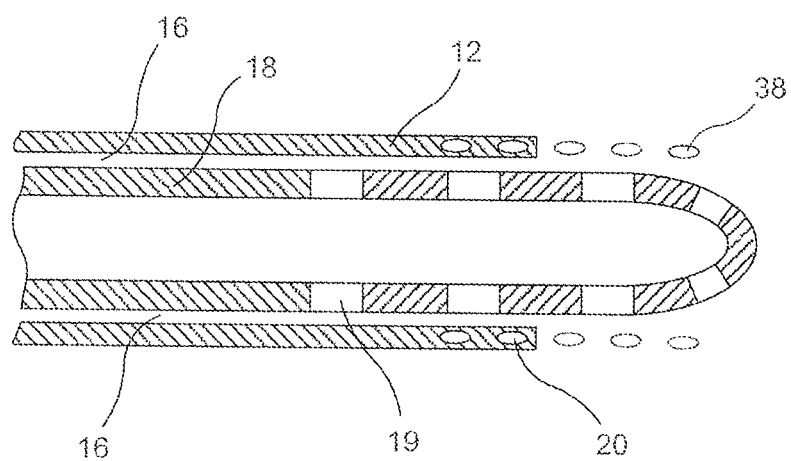

Referring now to FIGS. 1 and 2, a distal end 12 of a laser catheter 10 for atherectomy procedures in accordance with one embodiment of the invention is shown. The laser catheter extends between distal 12 and proximal 14 ends thereof and is formed with a central passageway 16, which receives a guide wire 18 inserted into the body lumen (e.g., vascular system) prior to catheter introduction. The passageway 16 can also be used to remove/evacuate occlusion debris from an area near the distal end of the catheter. The guide wire 18 facilitates the advancement and placement of the laser catheter to the selected portion(s) of the body lumen for laser ablation of tissue.

The working (distal) end 12 of the laser catheter is provided with a plurality of laser emitters 20 that emit energy and ablate the targeted tissue. The opposite (proximal) end 14 of the laser catheter is connected to a fiber optic coupler 22, which connects to a laser system or power source 24. The laser catheter 10 is formed with an outer jacket or sleeve having the ability to resist user-applied forces such as torque, tension, and compression.

In one embodiment of the invention, the distal end 12 of the catheter may be formed as an outer band with a plurality of optical fibers acting as laser emitters 20. An inner band forms the central passageway or tube 16 which receives a guide wire 18 and/or provides a potential conduit or passageway connected to an aspiration system, discussed in more detail below, for translocation of materials cut or ablated by the laser emitters.

The cutting means in this embodiment is a laser ablation means that includes laser emitters 20 embedded within a catheter. The energy emitted by the laser emitters 20 cuts, separates, and/or ablates the soft tissue, plaque build-up, calcium deposits and other types of undesirable lesion or bodily material within the subject's vascular system in a pattern substantially similar to that of the cross-sectional configuration of the laser emitters.

The light source 26 is an array of optical fibers 20 powered by a laser. The apparatus of the invention also includes an energy/power source in power communication with the light source and is adapted to provide power to the light source. The energy/power source 24 can be DC and/or AC. The apparatus can optionally be adapted to contain an autonomous energy source (e.g., batteries or the like). The energy source 24 is in power communication with the light source 26 via any conventional means, including cable(s). The apparatus further includes a controller or control unit 112 (see FIG. 3) that controls the amount (including duration) of the light that is applied to the treated area.

Figure 3:
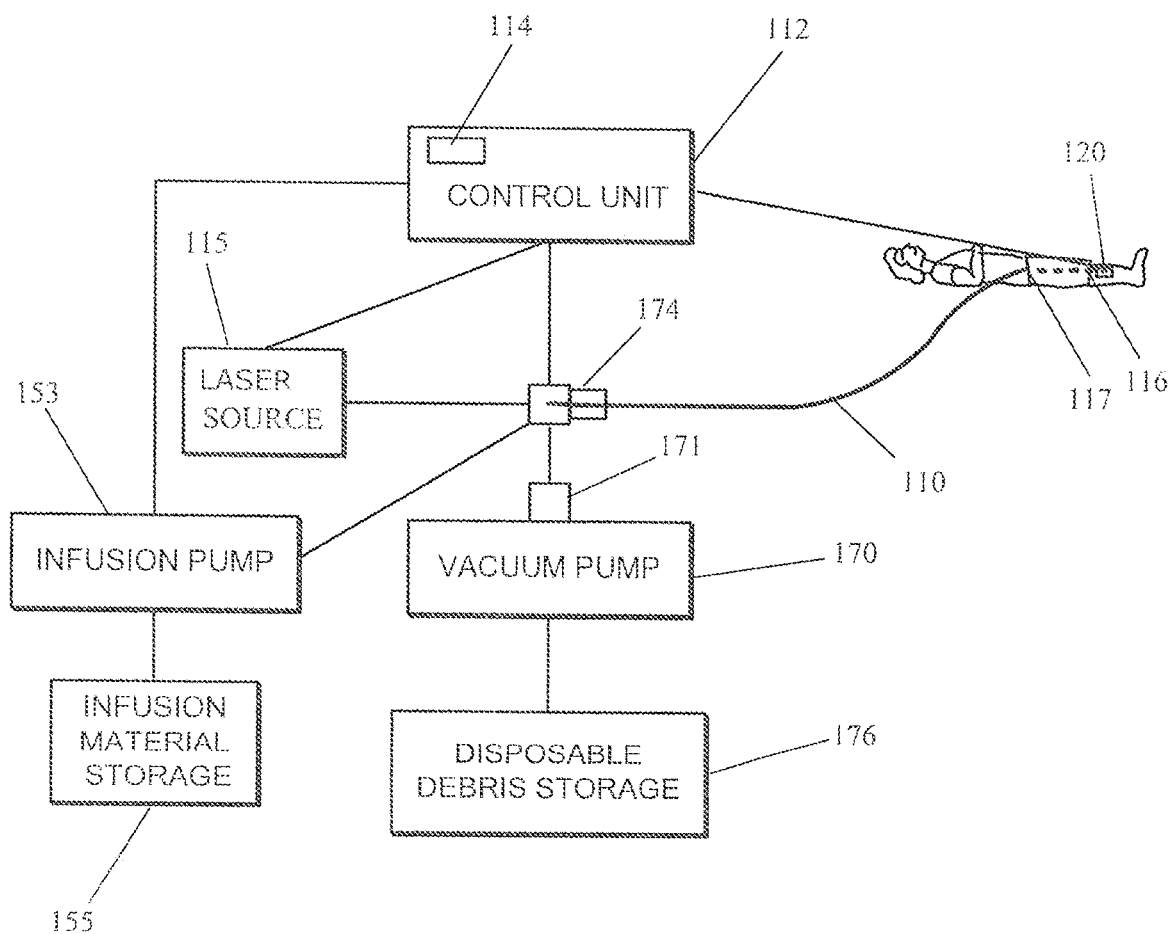
FIG. 3 is a diagram illustrating the system of the invention.

As illustrated in FIG. 3, the control unit 112 is provided to regulate the laser energy/power source 115 for the optimum output level and different characteristics of the laser light (such as wavelength, pulse duration, pulse shape, repetition rate etc.) based on type and characteristics of the targeted occlusion (hard, soft, blood, etc.) and/or characteristics of the catheter (length, diameter, temperature, etc.). Characteristics of the control unit 112 may be adjusted by the operator. As to the essential aspect of the invention, such characteristics can be manually or automatically adjusted based on the signals and data received from the sensors 32 and 34 (see FIG. 1) installed within the catheter.

As illustrated in FIG. 3 the control unit 112 houses a programmable logic controller 114 or microchip and laser power source 115 in operable communication to provide power and to control operation of various units of the system of the invention. The control unit 112 preferably comprises a base arranged so that the control unit may be stably supported on a work surface or a body surface during material removal operations. The control unit 112 also preferably incorporates control systems for actuating, adjusting and providing system information concerning laser power characteristics, axial translation, aspiration, infusion, which displays reading of sensors located at the distal end instrument and the like. The control unit may include, but not limited to laser power control unit, vacuum control unit, guidewire control unit, and aspiration and infusion control unit. The control unit 112 also controls a block providing information concerning operating conditions and feedback from the material removal site to the operator. By means of a computer or microchip 114 the control unit 112 utilizes inputs received from multiple sensors 32, 36, 116 located at the catheter 120 and/or other critical regions of the catheter assembly to continuously updated output to an operator including such operating parameters as laser parameters delivered to the treatment site, temperature at the material at removal site; advance rate; aspiration rate and/or volume; infusion rate and/or volume; and the like. Control unit 112 may additionally provide adjustable controls permitting the operator to control operating parameters of the material removal operation.

The control unit 112 is provided to regulate the laser power source 115 for the optimum output level based on type and characteristics of the targeted occlusion (hard, soft, blood, etc.) and/or characteristics of the catheter (length, diameter, temperature, etc.). Characteristics of the control unit 112 may be adjusted by the operator or automatically based on inputs from the sensors 116. Controlling various characteristics/parameters at the operation cite are based on the information provided by sensors positioned at the distal end of the catheter. Such characteristics can be manually or automatically adjusted based on the signals and data received from the sensors 16 installed within the laser catheter.

Sensors 32, 34, 116 may emit and receive various types of signals (optical, electromagnetic, acoustical, capacitance measuring) that will change parameters depending on the composition of the occlusion, so as to allow the control unit 112 to calculate and generate proper signals controlling operation of the laser source 115.

Detectors/Sensors 32, 34 located at the distal end 12 of the catheter (see FIG. 1) are able to recognize (determine) the physical and chemical composition of the occlusion. A computer or microchip 114 associated with the control unit 112 receives and analyzes information/data obtained by the sensors and generates signals to adjust parameters of the power source to optimize the destruction of an occlusion in the blood vessel and/or to produce other desired effect on targeted soft tissue.

According to one embodiments of the invention, sensors 32, 34, 116 are capable of detecting the level of hardness/calcification, water/moisture content, etc., within the material of an occlusion. As the tool/laser passes through various zones/sections/areas of the occlusion, optimal levels of laser radiation can be achieved for each zone of treatment. For example, a lower level of radiation and/or higher repetition rate can be provided for the destruction of calcinated occlusion having higher degree of hardness. On the other hand, higher levels of radiation and/or sower repetition rate will be generated and directed to the areas with softer occlusion materials. Laser power source may also be able to generate different wavelength or pulse duration irradiation optimized for the most optimal effect on the targeted tissue. The generated beam controllably destroys the occlusion as being absorbed in the target occlusion/tissue at the predetermined depths.

Sensors 32, 34, 116 may emit and receive various types of signals (optical, electromagnetic, acoustical, capacitance measuring) that will change parameters depending on the composition or other physical properties of the occlusion and/or tissue surrounding occlusion and/or physical characteristics of the catheter itself, so as to allow the control unit 112 to calculate and generate proper signals controlling operation of the catheter.

Sensors 32, 34, 116 located at the distal end of the catheter are able to recognize (determine) the physical and chemical properties of the occlusion. A computer or microchip 114 associated with the control unit 112 receives and analyzes information/data obtained by the sensors 16 and generates signals to adjust parameters of the laser power source 115 to optimize the destruction of an occlusion in the blood vessel and/or to produce other desired effect on targeted tissue. As an example, the control unit 112 analyzes information/data obtained by the sensors 32, 34, 116 and generates signals to adjust parameters of the laser power source 115 to optimize operation of the catheter. This includes also applying different physical mechanisms of action to destroy occlusion.

The sensors 32, 34, 116 are capable of detecting the level of hardness/calcification, water/moisture content, etc., within the material of an occlusion. As the catheter passes through various areas of the occlusion, optimal irradiation etc. can be achieved for each zone of treatment. For example, a higher level of irradiation can be provided for the destruction of calcinated occlusion having higher degree of hardness. On the other hand, lower intensity beams will be generated for the areas with softer occlusion materials.

Utilization of a laser in the present laser catheter is accompanied by automatic target feedback, thermal feedback for example, to precisely control the dosimetry of the laser irradiation. This is needed to prevent damage to surrounding tissue. An output of the non-contact thermal detector 136 [to be shown] can be used to adjust the output of the laser power source 115 to maintain selected characteristics including temperature at the treatment site.

Absorption of laser energy by the material of the occlusion may result in elevation in temperature of the surrounding tissue. In the invention, this occurs controllably without causing irreversible thermal damage to the surrounding tissue of the arteries. The laser control unit 112 adjusts the energy to maintain a pre-selected target temperature at the site/spot. In one embodiment of the invention, to maximize patient safety, an optional continuous or pulsed cooling device can be provided to deliver a coolant through the hollow guide wire to the operation cite during or after the laser procedure.

To further control the destruction occlusion, a condition of the entire artery body and/or the tissue surrounding the operation site is monitored by a detecting arrangement or detector 138 [to be shown] adopted to detect irradiation reflected from such tissue. One of the essential functions of the detector 138 is to control the effect of the energy or light source on the tissue surrounding the site. In every individual case, doctor sets specific characteristics of the irradiation to produce the required effect. If a situation at the operation site becomes unfavorable, for example the temperature exceeds predetermined limits, the detector 138 generates a signal directed to the control unit 112, which in turn produces a correcting signal to the power unit or to the control arrangement of the system.

The control unit 112 may be provided with a computer or microchip 114 capable to receive and analyze the information obtained by the detector 136 and to generate a control signal to adjust parameters of the laser power source 115 in such a way as to optimize the destruction of an occlusion in the blood vessel or other desired effect on targeted soft tissue.

In the invention to effectively control the destruction of the occlusion, a condition of the entire artery body and/or the tissue surrounding the operation site is monitored by the detector 117 adopted to detect irradiation reflected from such tissue. Particularly imaging detector 117 can be programmed to detect when the laser irradiation is accidently touches and thus reflect from the vessel walls. As one of the essential functions of the detector 117 is to control the effect of the procedure on the tissue surrounding the site, when contact of laser energy with vessel wall is detected the control unit stop the laser energy delivery to the treatment site to avoid damaging the healthy blood vessel wall tissue. In every individual case a doctor sets specific characteristics to produce the required effect.

The computer or microchip 114 of the control unit 112 receives and analyzes the information obtained by the detector 117 and to generate a control signal to adjust parameters of the power source 115 in such a way as to optimize the destruction of an occlusion in the blood vessel or other desired effect on targeted soft tissue.

In an alternate embodiment the control signal energizes special (cooling) arrangement (see above), so as to directly or indirectly lower/adjust temperature at the cite. Similar signals can be also produced when the prearranged levels of the energy density, power density or other characteristics of the operating laser are attained. This is necessary to exclude possibility of damaging an adjacent tissue. The detecting arrangement 136 can be made utilizing a wide variety of photoelements, photoresistors, photodiodes and other devices known in the art.

In an alternate embodiment the control signal generated by the thermal detector 117 energizes the cooling arrangement (see above) to directly or indirectly lower/adjust temperature at the site. This is necessary to exclude possibility of damaging an adjacent tissue. The detector 117 and the sensors 32, 34, 116 can be made utilizing a wide variety of photoelements, photoresistors, photodiodes and similar devices. Overheating may also occur in the length of the catheter particularly where the catheter is bended to sharp angle thus installing temperature sensors along the length of the catheter may improve safety profile of the device.

As discussed above, the material of the occlusion, as well as other factors may result in temperature elevation of the surrounding tissue. In the invention, the temperature elevation occurs controllably without causing irreversible thermal damage to the surrounding tissue of the arteries. The control unit 112 adjusts the energy to maintain a pre-selected target temperature at the site. In one embodiment of the invention, to maximize patient safety, an optional continuous or pulsed cooling device can be provided to deliver a coolant from the infusion material storage 155 by means of the infusion pump 153 through the hollow guide wire 18 to the operation site during or after surgical procedure.

The guide wire 18 (see FIGS. 1 and 2) utilized by the invention is formed as a hollow tube aiding navigation of the laser catheter 10 to the treatment site (e.g., through tortuous vasculature) using techniques known in the art. The laser catheter 10 travels alongside the guide wire 18, wherein at least a portion of the catheter is operatively coupled to the guidewire.

The hollow guide wire provides a further benefit and allows a central bore of the aspiration core lumen to remain unobstructed for delivery of coolant. An essential aspect of the guide wire 18 is that its hollow tube or central passage 16 is used as a conduit for aspiration of occlusion debris. As illustrated in FIG. 2, the guidewire 18 includes a plurality of openings/ports 19 along the distal end. Use of such hollow guide wire enables a clinician to catch occlusion debris 38 more efficiently, compare to the use of only the guidewire working channel formed in the central portion thereof. This is because, the openings/ports 19 allow to catch/collect debris 38 right at the site, where they are produced in the surgical procedure and before being disbursed. The hollow guidewire 18 can be made from metal, or plastic, or grafine or any other material which meets requirement for guide wire and is not permutable for liquid that contains debris of occlusion or embolus.

The multiple ports 19 facilitate a direct flow from both the side and the front of the suction conduit. When the devices of the invention are used to remove materials from the walls of a body lumen, embodiments having side openings 19 are preferable, because these side openings readily access target materials, avoiding having to bend the tip.

The hollow/tubular guide wire 18 of the invention, if needed, is also capable of delivering fluid/medication/coolant to a target location. With cuts/openings/ports 19 formed along at least a portion of the length of the tubular guide wires, the liquid/fluid/medication is allowed to leak from the bore of the guide wire out into the vasculature passageway. The location of discharge of liquid/medication/coolant from the tubular guide wire 18 can be controlled by controlling depth of the openings/ports 19 as well as the location thereof. In addition, a resilient/polymer sleeve may be inserted in the lumen or bore of a tubular guide wire, and/or on the outside as well, for sealing and preventing the outflow or discharge of liquid/fluid/medication from the guide wire lumen. Controlling the length of such sleeves on the guide wire 18 enables control of discharge points of liquid/medication/coolant from the guide wire. Furthermore, the exterior sleeve also provides better engagement/seal between the wire and the interior of vasculature, to assure proper position of a catheter inside the lumen walls.

In the method of the invention a clinician relies on the guidewire 18 for advancing laser catheters or other devices to treat a lesion within a patient's vasculature and to maintain the position of a catheter inside the lumen walls.

As to the aspiration aspect of the invention, a vacuum pump 170 (see FIG. 3 creates a low-pressure zone at the proximal end of the light catheter hollow guide wire to aspirate debris occlusion or embolus in the blood vessel. The diagram of FIG. 3 schematically depicts a system according to one embodiment of the present invention that may be connected to the passage of the catheter to evacuate the ablated or cored bodily material from a subject's vascular system using various embodiments of the catheter 110. In one embodiment of the invention the vacuum pump 170 provided at the proximal end of the system creates a low-pressure zone resulted in constant suction pressure within the lumen of a catheter to evacuate cut and/or ablated bodily material from a subject's vascular system. Obviously, the vacuum pump 170 provided at the proximal end of the system creates also a suction pressure within the hollow inner space of the guide wire to evacuate cut and/or ablated bodily material directly from the operating cite in the vascular system.

The diagram of FIG. 3 schematically depicts a system according to one embodiment of the present invention that is provided to evacuate the developed bodily material from a subject's vascular system using various embodiments of the catheter. The vacuum pump 170 provided at the proximal end creates low-pressure zone resulted in suction pressure to evacuate cut and/or ablated bodily material directly from the operating site in the vascular system.

In another embodiment, the vacuum pump 170 is interconnected to a pulse modulator 171, the actuation of which creates one or more pressure differentials to the aspiration system. Accordingly, in this embodiment rather than creating a constant suction pressure within the lumen of a catheter to evacuate cut and/or ablated bodily material from a subject's vascular system, the aspiration system of the invention applies alternative pressure(s), thereby creating pulses of suction pressure within the lumen. Utilizing a series of constant and/or varying pressure pulses is potentially beneficial in aspirating bodily material.

Aspirated liquid and/or particle from an area near distal end of the catheter are accumulated and stored in the disposable debris storage 176. A filter can be also provided upstream of system for filtering debris and aspirated bodily material and also for providing visual feedback to a user related to the type, quantity, and flow rate of material being removed from a patient. The debris storage container 176 may be in fluid communications with the vacuum pump 170 and may include one or more known devices for collecting and filtering materials removed from a patient. The debris storage container 176 may have transparent sidewalls for providing visual feedback to a user regarding flowrate, content, coloration, etc. Those of skill in the art will appreciate that various types of collection containers may be used. The collection container and/or filter may also comprise one or more custom filter features with various mesh sizes, capacities, etc. based on the specific application.

The distal end of the light catheter functioning as a suction conduit can be made of a variety of flexible or rigid materials or a combination of both To improve laser catheter resistance against kink-formation or against collapse under vacuum pressure, and to preserve flexibility in the meantime, the laser catheter exterior can be braided or woven with fibers made of materials such as metals or plastics. The distal end laser catheter conduit may have coatings on its inside or outside for various purposes, for example, for protection against corrosion by body fluids or for insulation against the high energy emitted towards its distal region. It can be of any dimension convenient for its intended use. Additional structures at the distal region may help prevent clogging of the suction conduit. For example, a filter, a screen, a mesh, a shield or other barriers can be provided at the distal region of the suction conduit.

Although the laser catheter 10 for atherectomy procedures has been discussed above, it should be noted that application of the laser catheter to many types of the intrabody surgery (as identified above) also forms a part of the invention. For example, in the ureteroscopy procedure, which treats and removes stones in the kidneys and ureters, the catheter 10 may be used in combination with the respective flexible scope. In the procedure doctor passes the scope with the laser catheter through patient bladder and ureter into kidney. Use of the laser catheter 10 may be especially applicable for larger stone removal, which passes through the scope to break stones up. Use of the catheter 10 is also applicable in the ureteroscopy for the removal of polyps, tumors or abnormal tissue from a urinary tract. Further application of the laser catheter of the invention is in percutaneous nephrolithotomy or percutaneous nephrolithotripsy, combined with a small tube to reach the stone and to break the stone up. After the procedure, the pieces of a stone are vacuumed up and removed from the system with a suction/aspiration arrangement of the invention.

Figure 4:
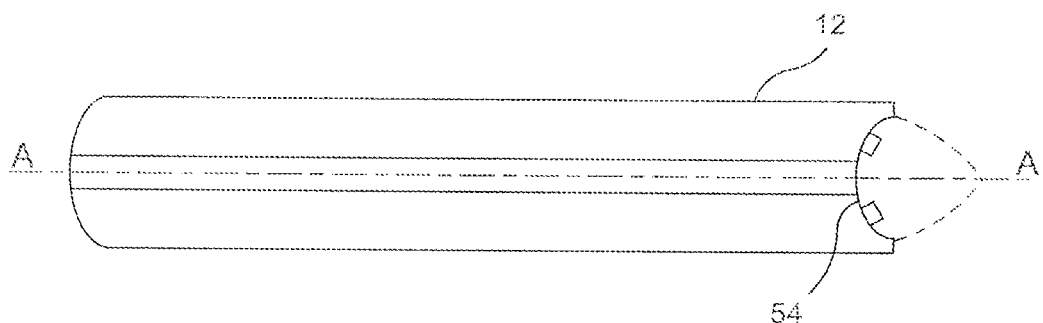
FIG. 4 is a diagram illustrating a distal end of another embodiment of the light delivery catheter.

As illustrated in FIG. 4, in a further embodiment of the invention the distal end 12 of the laser catheter is formed having convex-shaped region 54, which can be made of a resilient material. This feature is resulted in the following advantages to the invention.

An open convex-shaped (funnel shaped) cavity is formed to accumulate and catch debris from occlusion in front of the hollow light catheter channel used for aspiration of debris.

The convex-shaped region 54, focuses the light energy emitted from the distal end 12 of the light/laser catheter 10 to be optimally focused at the longitudinal axis A-A of the catheter and in the vicinity of the distal end. The light energy is projected along the catheter longitudinal axis A-A for optimal destruction of the occlusion. This minimizes the risk of undesirable damage from laser radiation to the walls of the body lumen (e.g., vascular system) and other adjacent tissues.

The resilient convex-shaped region 54 forms a suction cup which facilitates engagement between the distal end of the catheter and the occlusion, so as to prevent spreading and facilitate catching of the debris.

The convex-shaped region 54 of the laser catheter can be used in many types of the intrabody surgery (as identified above). For example, it can be used in ureteroscopy procedure, which treats and removes stones in the kidneys and ureters. The convex-shaped region 54 may be used in combination with the flexible scope, which is passed through patient bladder and ureter to provide an enhanced contact with kidney. Use of the convex-shaped region 54 facilitates larger stone removal, combined with a laser, which is passed through the scope to break stones up. Another example is use of the convex-shaped region 54 in the ureteroscopy for the removal of polyps, tumors or abnormal tissue from a urinary tract. Similar to the above discussed approach, the convex-shaped region 54 can be used in percutaneous nephrolithotomy or percutaneous nephrolithotripsy, combined with a small tube to reach the stone and break stone up with a laser or high-frequency sound waves.

In the invention lasers works on selective absorption of laser energy in the occlusion material. The absorption and effect on occlusion material depend on laser irradiation parameters including but limited to laser irradiation wavelength, pulse duration, repetition rate, energy in the pulse and/or energy fluence (density of laser radiation) delivered to the square area unit of the targeted material or surface.

As to an alternate embodiment, FIG. 4 provides an alternative way to deliver laser energy to the occlusion site by using diode lasers located and integrated right into the occlusion-facing end of the catheter. In such design the laser energy is produced right at the end of the catheter therefore eliminating the optical fibers used to deliver laser energy in other embodiments of this invention. Power supply wires are incorporated into the catheter under this design. Using laser diode can be a cheaper and more reliable way to deliver laser energy to the occlusion.

It is often difficult for a user to maintain sufficient control throughout both the advancement and removal of the catheter/guidewire. Conventional dispensers typically do not permit the catheter/guidewire to maintain fluidal/electrical connection throughout both the advancement and removal of the catheter/guidewire. Accordingly, it has been long felt and unsolved need to provide catheter dispensers which allow for safer handling and manipulation by enabling users to have increased control over the guidewire and catheter.

Figure 5:
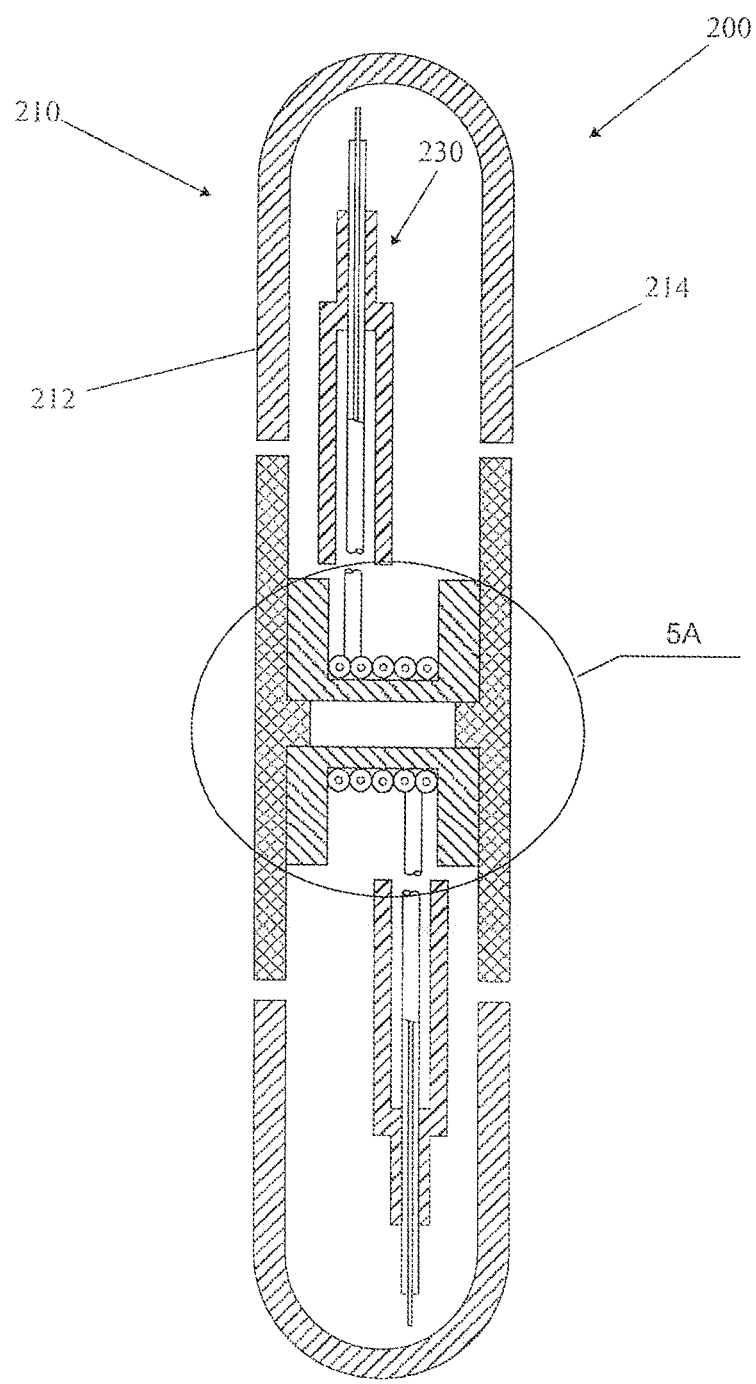
FIGS. 5 and 5A are a section views illustrating a combination of sterile packaging-dispensing device for a laser catheter.
Figure 5A:
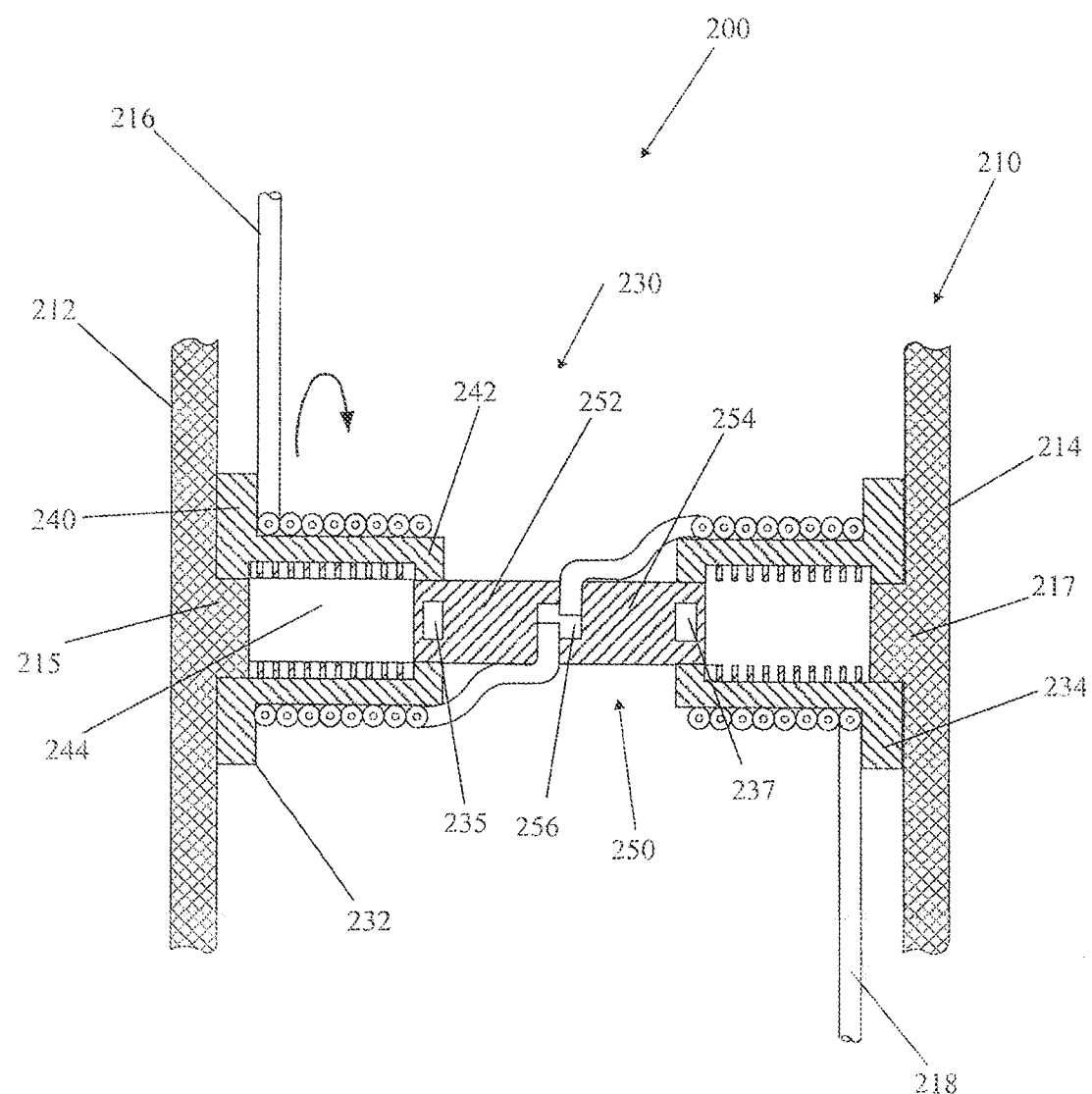

Referring now to the figures, FIGS. 5 and 5A that illustrate a combination 200 of sterile packaging-dispensing device for a laser catheter of the invention, wherein the catheter is wound on the reel dispenser rotatably disposed in the packaging interior. The combination is configured to safely store and dispense an elongated medical device such as laser catheters during surgical procedures and the like.

As illustrated in FIGS. 5 and 5A the package 210 of the invention is in the form of a pouch defined by at least first 212 and second 214 walls spaced from each other to define a receiving cavity 211 therebetween. Extensions 215 and 217 extend outwardly from central regions of inner surfaces of the respective walls. Purpose of the extensions will be discussed later in the application. In one embodiment of the invention each wall 212, 214 may comprise a layer of clear impermeable polymer. The two walls are sealed together at their edges to enclose the dispensing device with the catheter disposed within the receiving cavity. The hanging means (not shown) in the form of an opening can be provided passing through both walls in the vicinity of the sealed edges. In an alternate embodiment, to facilitate sterilization process, after the dispensing device is positioned within the package, at least one wall is formed as a layer of a semipermeable polymer.

Multiple ways of manufacturing the walls of the package are within the scope of the invention. For example, in one embodiment, the walls of the package can be thermally formed on a mold from a soft thermoplastic, such as styrene or polystyrene. In another embodiment, the walls can be injection molded. In another embodiment, the walls can be poured on a mold using a quick setting plastic or resin. Other methods of manufacture will be obvious to those of ordinary skill in the art having the benefit of this disclosure.

As previously discussed, the distal end of the laser catheter is provided with a plurality of laser emitters that emit energy and ablate the targeted tissue. The proximal end of the laser catheter is connected to a fiber optic coupler and the power source. For the purposes of the application a part of the laser catheter associated with the distal end is being further referred to in the application as a distal branch 216, whereas a part of the laser catheter associated with the proximal end is referred to as a proximal branch 216. An inner band forms the central passageway or tube which receives a guide wire and/or provides a potential conduit or passageway connected to an aspiration system for translocation of materials cut or ablated by the laser emitters.

As further illustrated in FIGS. 5 and 5A a combination 200 consists of a package 210 defined by the first 212 and second 214 walls forming an interior space 211 therebetween for receiving a dispensing apparatus 230. Referring now FIG. 5A which illustrates a preferred embodiment of the invention. The dispensing apparatus 230 provided for independently dispensing the distal 216 and proximal 218 branches of the laser catheter consist of at least first reel 232 and second reel 234 interconnected by the axel 250. Each reel consists of a flange 240 with a substantially cylindrical base 242, having a hollow interior 244, which extends outwardly therefrom. In their independent rotational motion, the reels 232, 234 are supported on one side by the package wall extensions 215, 217 and from other sides rotatably supported by the axel pins 235, 237. The axel 250 is provided with independently rotatable first part 252 and second part 254. A cavity 256 is formed at a central region of the axel at an interface between the first and second parts. The inner ends of the proximal 216 and distal 218 branches of the laser catheter are spirally arranged on the bases 242 of the respective reels 232, 234, so that upon being placed within the cavity 256 a reliable optical connection between the branches is maintained to assure continuous performance of the catheter.

Any known means for joining the laser catheter with a rotational base 242 of the reels 232 and 234 can be used, including any additional means that may be necessary for permitting the rotational to be rotated while preventing the catheter 12 from becoming tangled or misaligned. The dispensing apparatus of the invention can be configured to have a variety of sizes, as needed. For example, reels of different sizes may be used to accommodate varying lengths of catheters. Any suitable material may be used for the features of the reel dispenser. Preferably, the features of the reel dispenser are made of an impervious material, most preferably a plastic material. The catheter is coiled around the respective reels of the dispensing apparatus 230 and is configured to have a variety of lengths, as needed.

The packaging combination of the invention allows for laser catheters or other elongated medical device to be efficiently packaged into a compact, coiled orientation, so as to assure stability and protection, as well as to independently dispense various branches of the catheter to accommodate needs of a practitioner during surgical procedures.

A method of dispensing the laser catheter according to an embodiment of the present invention comprises opening the package through an opening provide at a top potion of one of the walls, so as to expose the distal end of the catheter, so as to facilitate introducing the distal region into a patient. By pulling the distal branch 216 of the catheter, the first reel 323 of the apparatus 230 is rotated relative to the walls 212, 214 of the package, whereby the distal region of the catheter and the emitters are advanced toward the patient. In this operation, a user preferably holds the package by one hand, while pulling the distal branch 216 of the catheter resulted in rotating the first reel 232. In this manner, the distal branch 216, which is wound around the base 242 of the first reel 232 advances from the reel and out of the apparatus 230 and the package, and into a subject.

On the other hand, in order to dispense the proximal branch 218 of the laser catheter, the package is opened through an aperture provided at a bottom potion of one of the walls, so as to expose the proximal end of the catheter out of the package. By pulling the proximal branch 216 of the catheter, the second reel 234 is rotated relative to the walls 212, 214 of the packages, whereby the proximal region of the catheter advanced toward the power base of the laser apparatus. Thus, the proximal branch 218 wound around the base 242 of the second reel 234 is advances from the base and out of the apparatus 230 and the package, for connection to the fiber optic coupler and the power source and the like.

Figure 6A:
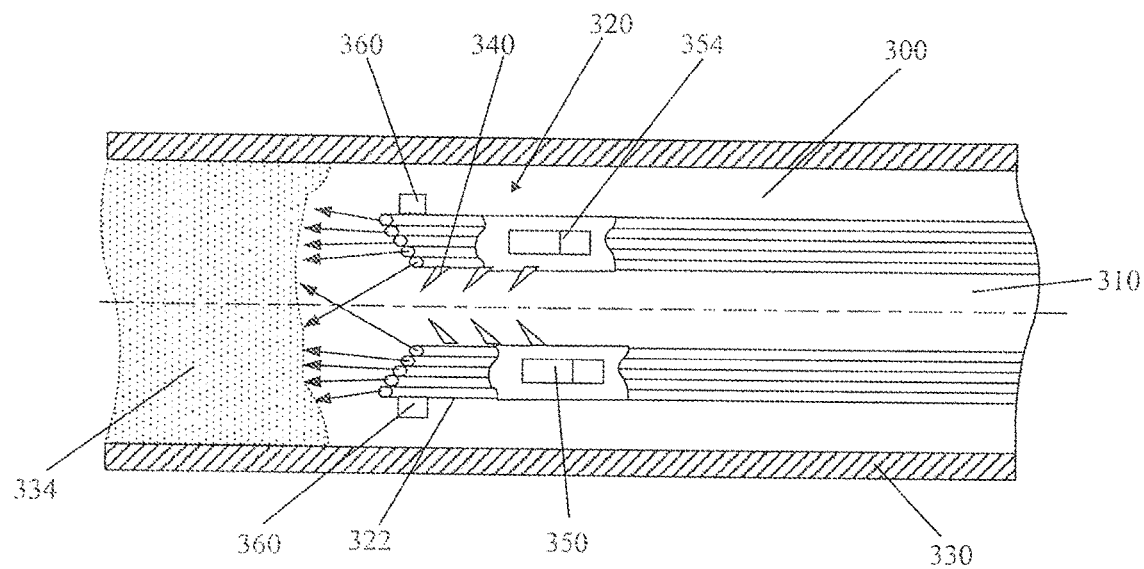
FIGS. 6A and 6B are diagrams illustrating an inflatable balloon used in the light delivery catheter.
Figure 6B:
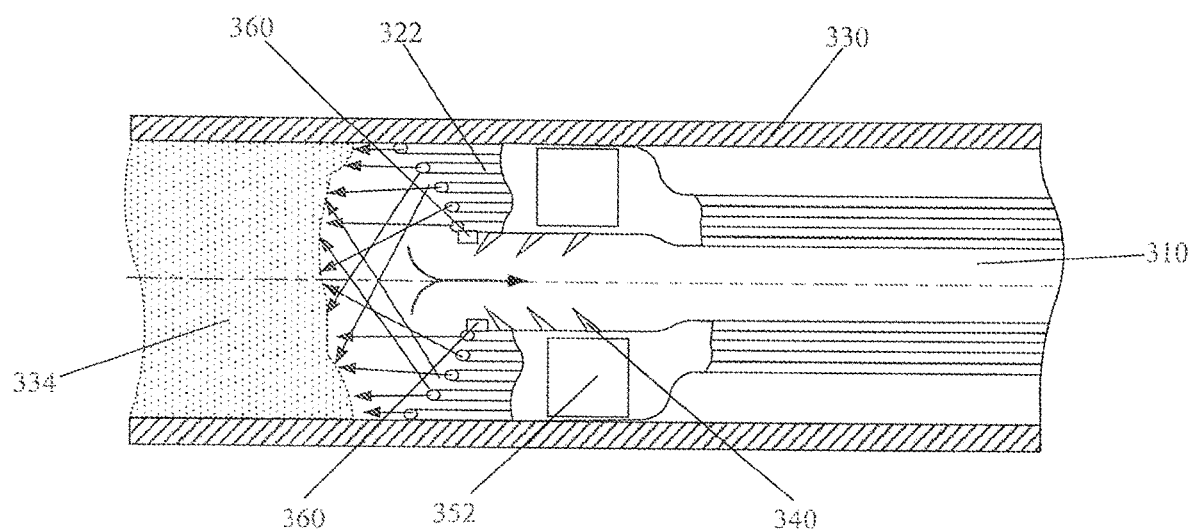

Referring now to FIGS. 6A and 6B illustrating another embodiment of the invention. The laser catheter 300 extends between distal and proximal ends thereof and is formed with a central passageway 310, which receives a guide wire inserted into the body lumen (e.g., vascular system) prior to catheter introduction. The passageway 310 can be also be used to remove/evacuate occlusion debris from an area near the distal end of the catheter. The guide wire facilitates the advancement and placement of the laser catheter to the selected portion(s) of the body lumen for laser ablation of tissue.

The distal end 320 of the catheter may be formed with one or multiple optical fibers 322 acting as laser emitters. The energy emitted by the laser emitters cuts, separates, and/or ablates the scar tissue, plaque build-up, calcium deposits and other types of undesirable lesion or bodily material within the subject's vascular system in a pattern substantially similar to that of the cross-sectional configuration of the laser emitters.

As illustrated in FIG. 6A distal end 320 of the laser catheter is inserted into a blood vessel 330 and located in the close proximity to the occlusion 334 blocking the vessel. The catheter is provided to deliver laser energy to the occlusion to destroy it into small pieces, so as to completely remove the occlusion and/or to form opening facilitating a free blood flow.

As previously indicated, in one embodiment for laser energy delivery the catheter is formed with one or multiple fibers 322 connecting the distal end 320 to the source of laser energy. Alternatively, the catheter can be fully or partially filled with a liquid which can serve as a medium to transfer the laser light from the source to the surgical site at the occlusion.

As illustrated in FIG. 6A, the distal end of the fibers 322 acting as laser emitters disposed proximally to the occlusion are arranged and shaped in such away so that laser energy optimally targets the occlusion for its destruction into the pieces of a predetermined size, as required by the optimal outcome of the procedure in view of the clinical purpose of the laser treatment. As illustrated in FIGS. 6A and 6B laser rays effectively and optimally cover the entire targeted area of the occlusion 334.

In the illustrated embodiment the catheter 300 is formed in such a way that after placement of the fibers the hollow central passageway 310 is formed along the longitudinal axis passing through a central region, as well as along inner walls of the catheter. The passageway 310 can serve as a channel for insertion of a guidewire. During the surgery a guidewire may be initially inserted first into the blood vessel and pushed through the vasculature to the occlusion site. Thin and flexible guidewire can be easily pushed through the complex vasculature. The hollow catheter can be then inserted over the guidewire.

The hollow passageway 310 in the catheter can also serve for the removal of the occlusion debris produced during the laser energy application to the occlusion. To facilitate the removal of the debris the negative pressure is created inside the hollow opening of the catheter.

As an optional feature, sharp blades 340 can be installed at the distal region inside the hollow passageway 310. Such blades are designed and positioned to facilitate further destruction of the debris initially developed during the laser-based occlusion destruction procedure. The initially produced debris in view of the suction are being forcefully directed against the blades to be further destroyed into a smaller piece that can be easily vacuumed through the catheter to the debris disposable area. The blades 340 oriented not to interfere with the use of the guidewire disposed in the catheter.

In order to facilitate insertion of the laser catheter 300 into the blood vessel the outer diameter thereof should be kept as small as possible (see FIG. 6A). This allows easy and safer delivery of the catheter through the patient vasculature to the occlusion removal site. However, the outer diameter of the targeted occlusion can be bigger than the initial diameter of the catheter. FIGS. 6A and 6B illustrate an alternative design of the distal end region of the catheter which is formed with an expandable arrangement 350 enabling the invention to optimally increase the outer diameter of the catheter and ultimately increase an area of the occlusion targeted by the laser energy for the destruction. While multiple expandable arrangements are within the scope of the invention, one of the preferred embodiments is shown in FIG. 6B. It is illustrated there that the distal end 320 of the catheter proximal to the occlusion is formed with an inflatable or balloon-type internal cavity 352 which is expandable upon delivery of pressurized gas by increasing pressure of a gas located within the cavity. There are many possible ways to engineer such arrangement which may be evident to a person of ordinary skill in the present art. As to one embodiment of the invention, the pressurized gas is delivered through a special design tube connecting the internal cavity or a balloon 352 to a source of such gas located at the proximal end of the catheter. As to another embodiment, the cavity 352 is separated into two or multiple chambers by a wall or barrier 354. Each chamber contains chemicals which are inert when separated, but expandable when combined. When the wall 354 is destroyed and chemicals come in contact with each other, a substantial volume of gas is produced inflating and substantially increasing volume of the internal cavity or a balloon 352. In use the barrier 354 separating those chemicals are remotely destroyed to combine the chemicals together and creating an extra volume of pressurized gas that expand the balloon cavity to the require size There are many technically feasible ways to destroy or puncture the barrier 354 between two chemicals including but not limited to inducing electric current into the barrier wall, so as to generate heat capable of destroying the barrier. Another way is to deliver an electric current through a wire incorporated into the catheter, wherein the current destroys the barrier. Alternatively, the current delivered through the wire incorporated in the catheter can elevate a temperature of the gas already pre-stored in the balloon cavity, so that the gas volume is expanded to the required condition, etc.

In the embodiment of FIGS. 6A and 6B one or more sensors 360 designed to analyze the physical characteristics of the occlusion and the surrounding area may be incorporated at the proximal to the occlusion end of the catheter. The signal from such sensors is delivered to the laser system control unit which optimally controls and manages the parameters of the laser system based on such sensor input including but not limited to temperature, density of the occlusion (soft, hard, etc.) as well as imaging sensors that can decipher type of the tissue located on the way of laser energy in order to prevent applying laser energy to the walls of the vessel.

In the embodiment of FIG. 6B upon inflation the cavity 352 expands radially in the direction from the center passageway 310 towards the inner walls of the blood vessel 330. In the embodiment of FIGS. 8A, 8B, 9A, 9B and 9C in addition to the cavity 352 which expands radially, an inflatable extension 370 is provided to expand longitudinally in the direction of the occlusion 354 along a longitudinal axis of the catheter 300. A cutting arrangement in the form of blades 380 is provided at the distal end of the extension 370. The cutting arrangement is released and moved towards the occlusion when the extension 370 is inflated. The inflatable extension 370 extends along the periphery of the cavity 352 with at least one or multiple blades 380 provided at an outer end of the extension. The blades 380 may be disposed at any part of the distal region of the catheter facing the occlusion 334, so as to be separated from or intermingled with the fibers 322. However, in the illustrated embodiment the blades 380 are disposed spaced from the fibers 322 in the vicinity of the outer surface of the cavity 350. Using a wire 382 or any other control arrangement a doctor can selectively activate, by means of the inflatable extension 370, single or multiple blades to engage, cut and destroy a predetermined area of the occlusion. The extension 370 can be formed integral with or separated from the main cavity 352, so as to be activated/inflated together with or separately from the main cavity. It is illustrated that the extension 370 is formed with an independent barrier/wall 372 which can be independently punctured when a mixture of multiple chemicals is used for its inflation in the manner similar to the above-discussed. In the embodiment of FIGS. 9A and 9B the blades 380 are separated from each other. On the other hand, FIG. 9C shows a unitary blade 385 in the form of a ring with an exterior sharp edge 386. Upon activation of the inflatable extension 370 the unitary blade 385 is pushed out and the circular exterior sharp edge engages the entire periphery of the occlusion. As previously discussed, the passageway 310 is used to remove/evacuate occlusion debris from an area near the distal end of the catheter.

Figure 7:
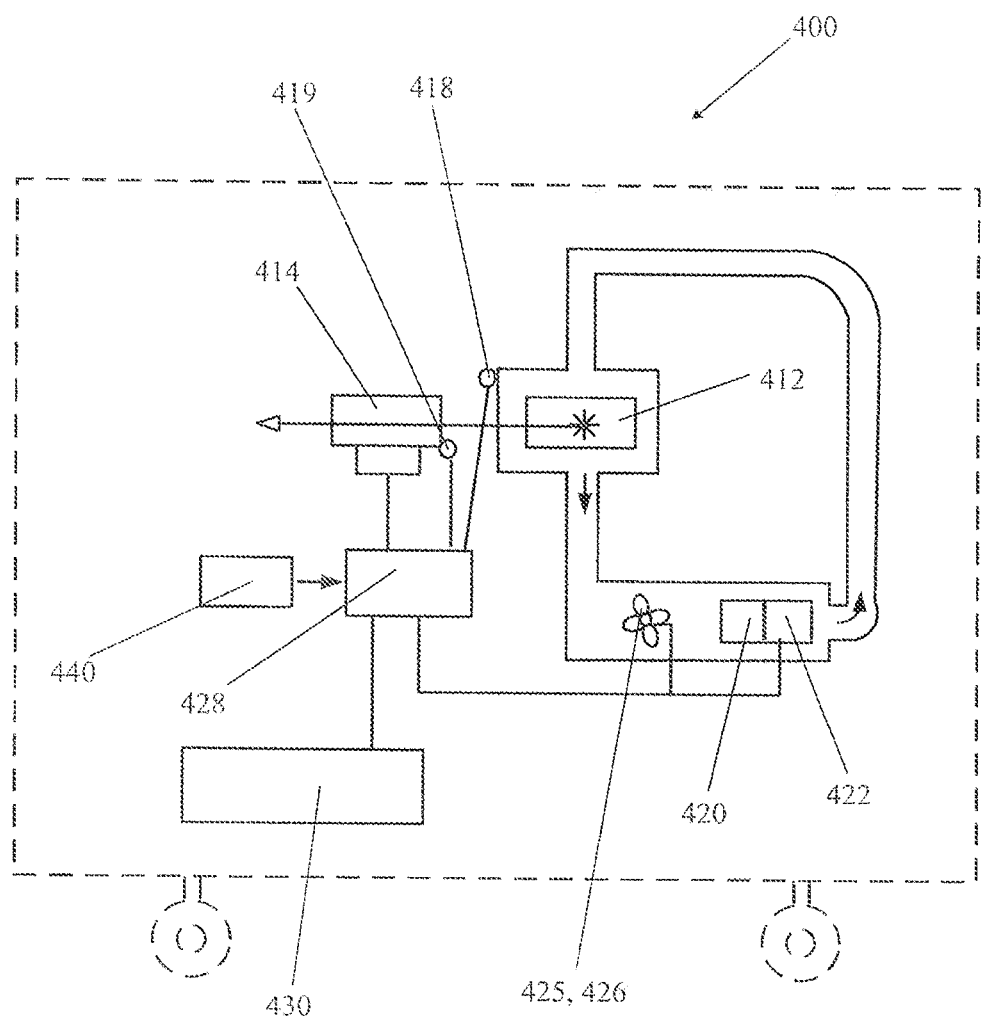
FIG. 7 is a diagram illustrating a motion sensor activation system of the invention.
Figure 8A:
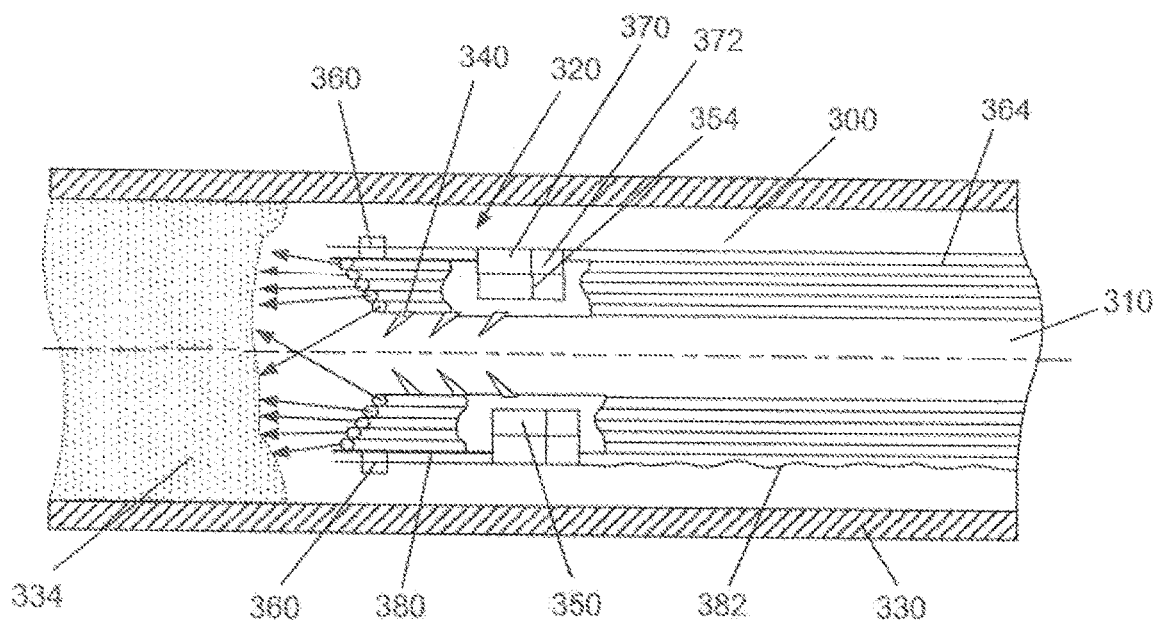
FIGS. 8A and 8B are diagrams illustrating application of a modified inflatable balloon combined with extendable blades.
Figure 8B:
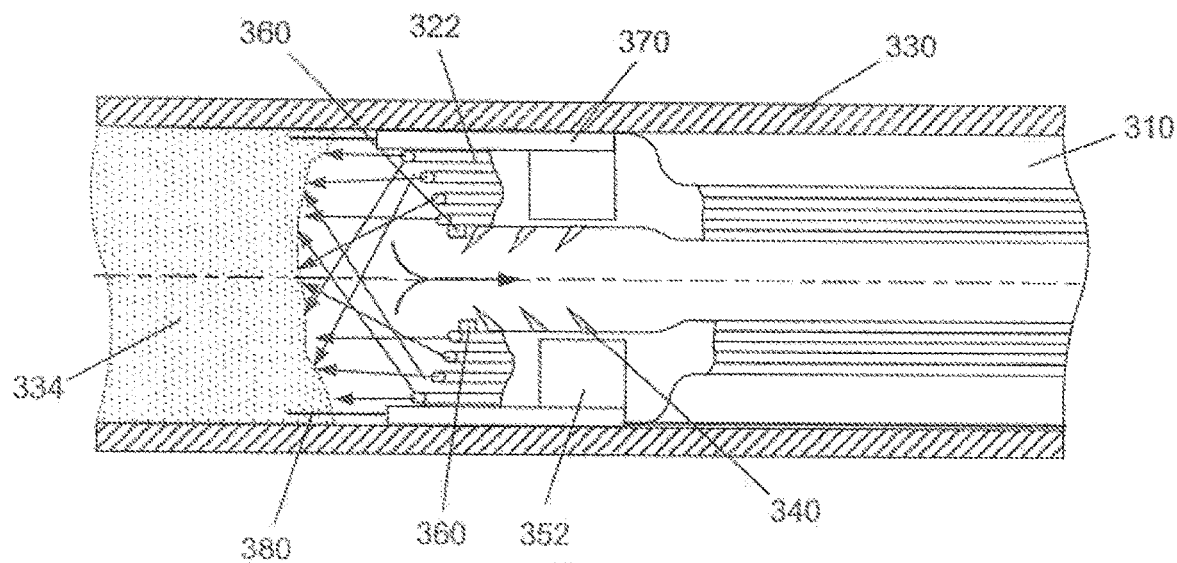

We are referring now to FIG. 7 which illustrates a further subsystem 400 forming a part of portable laser atherectomy device and certain functional elements integrated into a mobile design having any conventional motion arrangement 410, such as wheels, etc. Key components of the laser energy generation system, such as laser crystals/laser emitters 412, 414 are shown in FIG. 7. Laser system may have multiple laser generation elements for laser generation, amplification, and/or adjusting laser irradiation parameters as wavelength, pulse duration, polarization etc. as required for the optimal clinical effect on the treated tissue (soft, hard, or organ tissue).

For stable generation of desired laser parameters laser crystal and/or laser generation elements 412, 414 are required to be within certain predetermined range of physical parameters including but not limited to temperature, moisture etc. To achieve this parameter the laser crystal/laser emitter element 412, 414 are equipped with sensors 418, 419 to record temperature, moisture level or other physical characteristics of the laser crystal/laser emitter element. Further a heating and/or cooling elements 420 and 422 are provided to adjust temperature of the laser crystal/laser emitter elements 412, 414 by heating or cooling it. The signal from the sensors 418, 419 is supplied to the control unit 428 which through an application of a computer program controls operation of the heating and/or cooling elements 420, 422. In one embodiment the heating/cooling arrangement 420, 422 can be built as a water/air circulating loop which include the piping system 425 and pump 426. Open contour air cooling system can be also used and is preferred because of the simplicity and reliability. Alternatively, cooling elements 420, 422 can include a direct electronic powered heating/cooling arrangement. Battery 430 is provided for supply of electric power needed for the operation of the above discussed laser system.

The minimum preparation time to readiness of the laser device is critically important during surgical procedures. This is because laser intervention during surgery may be needed any time and often deviates from the initial plan of the surgery. Preparation time for readiness may comprise or be dependent on multiple lasers functions including but not limited to warm-up time, calibration time, etc. Laser device may be located within the surgery room and sometimes it can be located in a separate storage. Optimal management and control of the heating/cooling elements 420, 422 may play an important role in minimizing the preparation time to readiness of the laser device. During the inactive (storage) period heating/cooling elements # may be programmed to keep the laser crystal temperature (other spec) within optimal range to prevent any deterioration of those crystal through accumulation of water from air moisture condensation on the crystals. It is also essential to keep the laser crystal temperature within the set range allowing quick warm-up time for the actual surgery operation. In the embodiment of FIG. 7 laser system 400 is formed with a motion sensor 440 provided to activate the preparation protocol to surgery operation level laser crystal warm-up mode. Thus, as soon as the laser is moved and the motion sensor is activated, the system starts preparing itself for the surgery. This allows the laser system of the invention to prepare itself into the surgery operation mode even while it is only moved from the storage to the surgery room. In addition to a warm-up step, the other preparation to readiness steps can be activated by the motion sensor # and control unit including self-calibration etc. The control unit # can be equipped with remote control functionality through Wi-Fi, internet, radio waves or other means of remote or wireless communication. This allow operator to remotely control the unit, including launching a preparation to readiness mode immediately when the surgery may require. Remote controls also allow monitoring the laser system parameters including the battery level to arrange its recharge when necessary.

Referring now to the embodiment of FIGS. 10 and 10A illustrating a laser light assembly which consists of a hand-held device 740 and laser light device 700. The laser device 700 is formed by a tubular shaped body 702 having a hollow interior and consisting of a proximal part 704 and a distal part 706. The proximal part 704 is typically substantially longer than the distal part 706. A laser light transmitting fiber 708 passes through a central area of the hollow interior 710 of the tubular shaped body 702. The fiber 708 can be a single fiber or a bunch of multiple fibers put together. The hollow space between the fiber 708 and inner wall of the body is used for evacuation of debris produced during the surgical procedure. To retain the fiber 708 in its central orientation multiple retaining elements 712 are installed through the length of the hollow interior 710. Each element 712 is formed with a central open area 714 and a plurality of rays 716 extending outwardly therefrom. In the assembled position the fiber 708 is supported by and passes through the central open area 714 of each spreading elements 712. The rays 716 extending to the inner wall of the body 702 stabilize position of the spreading element and the fiber within the hollow interior 710. The segments 719 of the hollow body interior separated by the rays define multiple longitudinal channels used for evacuation of debris from the surgical site as well as for the delivery of various fluids facilitating the surgery. The proximal part 704 is typically made from a rigid material, whereas the material used in manufacturing/production of the distal part 706 is resilient and capable of being bent or deformed. As further illustrated in FIG. 12A, a hollow conduit 720, extends at the exterior of the body 702 along its longitudinal axis between closed 721 and open 725 ends thereof. A flexible element or string 722 is positioned within a hollow interior space and is attached to the closed inner end 721 of the conduit. The opposite free end the string extends from an open end 725 of the conduit and can be manipulated, pulled by a doctor during the procedure. To simplify the string manipulation, as it shown in FIG. 12, the free end of the string 722 extends to the hand-held device 740 which is typically positioned in the hand of a doctor during the surgical procedure. A resilient member 726, such as a spring for example, is positioned at the distal part 706 oppositely to the conduit 720. In use by pulling the string 722 a doctor can remotely manipulate and/or bend the resilient distal part 706 and the fiber 708 positioned inside to an optimum angle, thus targeting the distal end into required direction within the patient's body lumens. When manipulation of the resilient distal part 706 and the respective part of the fiber 708 is no longer required, the string 722 is released by a doctor at the hand-held device 740 and the spring 726 returns the resilient distal part to its original orientation.

Referring now to FIG. 11 illustrating a laser surgical system 500 according to a further embodiment of the invention. A connecting arrangement 510 extends between proximal 512 and distal 514 ends, with the proximal end being connected to a laser source 516. In one embodiment a pump 518 can be provided at the proximal end 512 to generate a vacuum. In another embodiment the vacuum pump 518 is connected to a hand-held surgical device 520. A control mechanism can be added to the system to modulate the intensity of the vacuum. The hand-held surgical device 520 containing controls and a disposable light guide or laser surgical instrument 525 is provided at the distal end 514 of the connecting arrangement. The connecting arrangement 510 can be formed as a hollow articulated arm or can be in the form of flexible fiber delivery guide. In the embodiment where the articulated arm is a light delivery system, the light is guided from the laser source 516 to the point of application at the laser surgical instrument 525. In the other embodiment the connecting arrangement combines an energy-transmitting means including flexible fiber with the suction producing pump 518 to enhance the efficiency of material removal from a body lumen through the hollow space inside the arms. In the latter embodiment the hollow interior of the connecting arrangement may include a suction conduit and a high-energy conduit. The hand-held devices similar to that of the invention are known in the art and do not form a part of the invention. An outer part of the hand-held device 520 accommodates a disposable laser surgical instrument or energy-transmitting conduit 525 formed with a light delivery tip 526 at its distal end. Delivery of the disposable laser surgical instrument 525 to the treatment site is facilitated by a guide 530.

As illustrated in FIG. 11, a resilient, disposable funnel-shaped guide 530 comprises a generally truncated cone or pyramid shaped hollow body 532 defined by a peripheral wall 534 extending between a larger input region 536 having a larger cross-section and a narrow outlet region 538 having a smaller cross-section. The outlet region 538 is typically sharp with a small opening 539 to accommodate passage of the light delivery tip. The wall 534 is centered on a longitudinal axis extending through the guide 530. A cut out section/portion 540 extends longitudinally within the peripheral wall 534 between the input and output regions. In use, upon insertion of the laser surgical instrument or energy-transmitting conduit 525 into the hollow body 532 the peripheral wall 534 expands/spreads apart at the cut out portion 540 enabling the light delivery tip 526 to pass through the guide interior and to extend outwardly from the opening 539 of the output region. The guide can be made of an inexpensive, resilient, but firm enough material to assure tissue penetration, and to simplify a sterilization process. Various plastics can be used for this purpose, making the guide 530 disposable to accommodate needs of each individual patient.

In use upon manipulation by a doctor, the guide 530 is inserted through the muscles, ligaments, bone tissue, etc. of a patient's body, so that the outlet end 538 is positioned in the vicinity of the treatment site 550. Then the laser surgical instrument or energy-transmitting conduit 525 is inserted into and/or pushed through hollow body 532 defined by the wall 534, causing the wall to expand at the cut-out portion 540 enabling the light delivery tip 526 to pass through the output opening to be positioned at the treatment site 550. Engagement between the light delivery tip 526 and the output opening 539 stabilizes position of the surgical instrument at the treatment site. The laser surgical instrument including the light delivery tip 526 can vaporize tissue if the tip is in contact with the tissue or coagulate tissue if the tip is spaced away from the tissue. When the pump 516 is provided at the proximal end 512 of the articulated arm, the debris produced during the surgery are evacuated from the treatment site through open area between the wall of the arm and the light guide or fiber.

In the embodiment of FIG. 11A the laser surgical instrument 525 is in the form of previously discussed tubular shaped laser device 700. Manipulation of the resilient distal part 706 is conducted by a doctor who operates the string 722 extended to the hand-held device 520.

Figure 12:
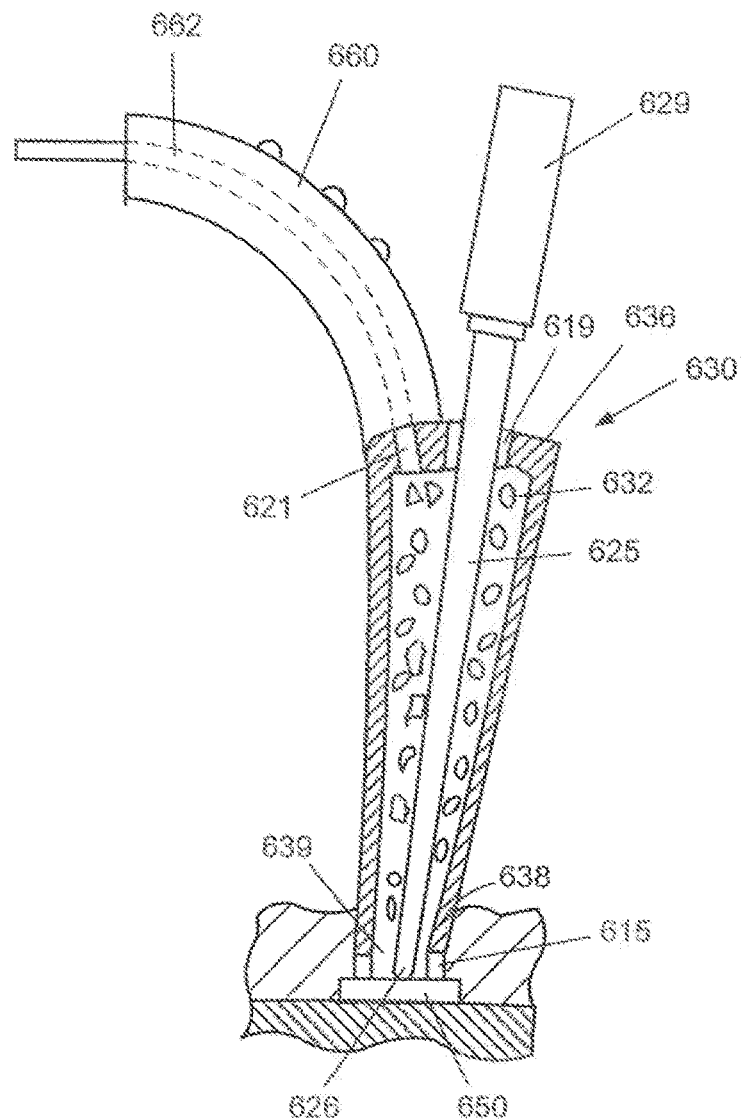
FIG. 12 is a view illustrating a laser surgical device according to still further embodiment of the invention.

Referring now to FIG. 12 illustrating a modified version of the guide 630 used in combination an endoscope or a viewing instrument 615 and the laser surgical tool or energy-transmitting rod/conduit 625 formed with a light delivery tip 626 at its distal end. In a manner similar to the above-discussed FIG. 10, the body of the guide 630 is configured as a truncated cone or a pyramid defined by a peripheral wall extending between a top input region 636 having a larger cross-section and a narrow outlet region 638 having a smaller cross-section. A hollow chamber 632 is formed within the body interior. A top area of the input region is formed with a first aperture 619 adapted to accommodate and guide motion of the energy-transmitting rod and a second aperture 621. A handle 660 is formed with a suction conduit 662 extending outwardly from the top input region. The suction conduit is connected at its proximal end to a pump that creates a vacuum and its distal end coincides with the second aperture 621. Suction caused by the vacuum pump through the conduit 662 connected to the hollow chamber facilitates evacuation of debris produced during the procedure from the treatment site 650 through the chamber and the conduit. Additional structures provided at the conduit 662 may help prevent clogging of the evacuation system. For example, a filter, a screen, a mesh, a shield or other barriers can be molded onto or otherwise attached to the conduit 662 or any other suitable area. The outlet end 638 is substantially sharp and is formed with a small opening 639 to accommodate passage of the light delivery tip 626. A cut out portion, similar to the previously discussed portion 540 may extend longitudinally within the peripheral wall.

Detection of the light delivery tip movement inside a body lumen is accomplished through the viewing instrument 615. An example of a viewing instrument is an endoscope that contains a fiber optic illumination source and a fiber optic lens for viewing to enable the doctor to view a surgical area 650.

In use, upon insertion of the laser transmitting rod 625 with a light delivery tip 626 through the first aperture 619 of the input region into the hollow interior, the light delivery tip passes through the guide interior 632 to extend outwardly from the opening 639 of the output region, so as to be positioned in the vicinity of tissue at the surgical site 650. Light delivery tip 626 can vaporize tissue if the tip is in contact with the tissue 650 or coagulate the tissue if the tip is spaced away from the tissue. By moving the handle 629 forming a part of the rod, a doctor can remotely manipulate the laser transmitting rod within the aperture 619, so as to position the light delivery tip 626 to an optimum angle, thus targeting the tip into a required direction within the patient's body lumens.

What is claimed is:

1. A laser surgical guide system for guiding a laser surgical instrument comprising:
   a guide arrangement formed by a wall shaped as a truncated cone defining a hollow body extending between an input region and an output region, a cross-section of the input region being greater than a cross-section of the output region, an output opening provided at the output region, a cut out portion extending longitudinally through the wall of the body between the input and output regions, a top wall extending through the input region and having at least first and second apertures, a chamber formed within the hollow body, the first aperture guiding passage of a laser surgical instrument having a light delivery tip, a handle connected to the second aperture and extending outwardly from said top wall, a suction conduit connected to the chamber through the second aperture and passing through said handle, a proximal end of the suction conduit connected to a vacuum device creating a vacuum at a distal end thereof and within the chamber, and
   wherein in use upon insertion of the laser surgical instrument through the first aperture into the chamber the light delivery tip through the output opening is positioned at a treatment site; wherein said vacuum causes evacuation of debris produced at the treatment site through the output opening, the chamber and the suction conduit.

2. A laser surgical guide system of claim 1, further comprising additional devices provided at the suction conduit to prevent clogging of evacuation system.

3. A laser surgical guide system of claim 2, wherein said additional devices are selected from the group comprising a filter, a screen, a mesh, a shield and other barriers associated with the conduit.

4. A surgical guide system of claim 1, further comprising a viewing instrument provided at the output region.

5. A laser surgical guide system of claim 4, wherein the laser surgical instrument is a laser transmitting rod, by manipulating the laser transmitting rod within the output opening the light delivery tip is positioned to an optimum angle at a patient's body lumens while being observed by the viewing instrument.

6. A surgical guide system of claim 1, wherein said top wall is integral with the input region.

* * * * *